United States Patent [19]

Frangi

[11] Patent Number: 4,671,264
[45] Date of Patent: Jun. 9, 1987

[54] PROCESS FOR MAKING PANTS-LIKE UNDERGARMENT INCORPORATING A PARTIALLY RIGID AND PARTIALLY ELASTIC STRUCTURE FOR RETAINING ABDOMINAL TISSUE IN PLACE, PARTICULARLY FOR RETAINING INGUINAL HERNIAS IN PLACE AND PANTSLIKE OBTAINED WITH SUCH PROCESS

[76] Inventor: Giampietro V. Frangi, Via Crispi 1, 21100 Varese, Italy

[21] Appl. No.: 574,904

[22] Filed: Jan. 30, 1984

[30] Foreign Application Priority Data

Jan. 31, 1983 [IT] Italy ............................... 83605 A/83

[51] Int. Cl.$^4$ ............................................. A61F 5/24
[52] U.S. Cl. ..................................... 128/96; 128/99; 128/100
[58] Field of Search ...................... 129/96, 99, 100, 95, 129/101, 98; 2/400, 401, DIG. 7

[56] References Cited

U.S. PATENT DOCUMENTS

| 3,294,086 | 12/1966 | Nelkin | 128/96 |
| 3,454,003 | 7/1969 | Kleber-Sailhen | 128/96 |
| 3,486,501 | 12/1969 | Erickson et al. | 128/96 |
| 4,059,103 | 11/1977 | Glaser | 128/96 |
| 4,351,325 | 9/1982 | Walker | 128/96 |
| 4,416,272 | 11/1983 | Nelkin | 128/96 |

Primary Examiner—Gene Mancene
Assistant Examiner—J. Hakomaki
Attorney, Agent, or Firm—Gifford, Groh, VanOphem, Sheridan, Sprinkle and Dolgorukov

[57] ABSTRACT

A combination underpant and herial truss includes an underpant brief, an elastic belt disposed at the circumferential upper edge of the brief, and a pair of at least partly elastic bands whose ends are affixed to the elastic belt. The bands pass laterally of the crotch of the pant, adjacent the leg holes of the brief. Preferably, the bands include a first inelastic segment on the front of the underpant extending diagonally across a hernia affectable region of the wearer, a second strongly elastic segment disposed adjacent the inguinal channel of the wearer, a third inextensible segment extending upwardly from the second segment, and a moderately elastic fourth segment connected to the belt and the third band segment. Pockets are included over the hernia affectable region for receiving a retaining pad.

16 Claims, 4 Drawing Figures

PROCESS FOR MAKING PANTS-LIKE UNDERGARMENT INCORPORATING A PARTIALLY RIGID AND PARTIALLY ELASTIC STRUCTURE FOR RETAINING ABDOMINAL TISSUE IN PLACE, PARTICULARLY FOR RETAINING INGUINAL HERNIAS IN PLACE AND PANTS-LIKE OBTAINED WITH SUCH PROCESS

BACKGROUND OF THE INVENTION

1. Field of the Invention

The present invention relates to a process for making pants-like undergarment, serving as a truss, incorporating a partially rigid and partially elastic intersewn structure, for retaining abdominal tissue in place, particularly for retaining inguinal hernias and to a pants-like undergarment, serving as a truss, obtained with such process.

2. Description of the Prior Art

Elastic pants-like undergarments, serving as a truss, for retaining abdominal tissues, including an ample and strongly elastic intersewn structure have been known before. The effectiveness of these pants-like undergarments, serving as a truss, and of their structure was rather dispersed. In fact, such known pants-like undergarment involves with its less effective sections substantially the whole abdomen, extending downwardly, even under the groin.

Such dispersion was detrimental to a specific effectiveness within the critic region, whereas in different conditions it disturbs the operation of covered organs of the body. Consequently, instead of a remedy, favourable conditions for the appearance of disease aimed to be recovered are provided. In fact, a known pants-like undergarment, serving as truss, comprises a belt, involving the upper abdominal area, i.e. over the hernia affectable critical region and involving an elastic strip, having an average width of about 12 cm, whose upper section is made of very thick elastic material. This arrangement was provided in the aim to increase the supporting effect. This could be correct for normal typical, anatomical, subjects but not for users affected by disease needing the use of pants-like appliance. Quite often the users are fat, corpulent and have the region of their bodies, to be involved by truss, strongly bevelled, thus a sliping down and a rolling up of the appliance, may easily occur. Considering that this appliance is to be produced in series, and to be adapted for typical users, having standard sizes, as well as that the hernia affectable critical region is relatively of constant size and shape, it may happen that the known pants-like appliances are refused by such parts of the body not in agreement with their shapes, whereby the appliances gather together and when the refuse is thorough, due to the weakness of the elastic the garments slip down. And this is not a good service for appliances whose aim is to support bodies. In fact, only a reduced number of users have a well shaped waist, whereby the upper belts rest upon the hip-bones by preventing them to slip down. At any rate, the gathering of more than one thickness of rolled up or multiply pants-like provides at least a disturbance for the user.

SUMMARY OF THE INVENTION

The aim of the present invention is to eliminate the aforesaid disadvantages and to offer, furthermore various advantages. The inventor, with ingenious perception, has conceived a pants-like undergarment, serving as a truss, strictly involving the very hernia affectable critical region, thus having substantially the shape of pants comprising an intersewn structure, partially elastic and partially inextensible, adapted to provide optimal retaining and suspending conditions, without involving outsider areas i.e. not included in the hernia affectable critical region. The pants-like undergarment, involving the hernia affectable critical region, substantially includes a wide, elastic, involving belt and two undercrotch trusses extending upwardly, across the belt, the former comprising elastic and inextensible segments, wherein the total extension and particular elasticity, are provided, by intercalation, therealong, of elastic and inextensible segments, by adjusting their lengths, instead of adjusting their elastic tension and the whole extension on the whole undercrotch. Moreover, once taken into account the elasticity of undercrotch segments, which are substantially the inguinal ones, i.e., the forward ones, which consequently are not limited to any thickness, the remaining sections and/or components e.g. those covering the glutaei and those, which in the front side cover the upper inguinal channel, may be made by inextensible cloth or fabric providing abundant comfort. This intersewn structure, is functionally distributed thereabout, so as to provide pants-areas with covering function which can be provided with an anatomic shape e.g. in the areas corresponding to the glutaei, as well as for provision of a genital bag, connected thereto, but functionally independant, possibly with suspending effect and anatomically shaped too. Thus, it not only provides effectively the retaining function but provides even substantially standard pants giving to the user substantially the same comfort of non-truss conventional pants. In fact, access to genitals is at once gained and the same may be extracted, with abundant facility, to provide usual physiological functions without affecting the supporting task of the pants which, being independent, do not stress the genitals. Corollary to such perception are particular arrangements, such as the distribution of sewings, reinforcements, consistency of contour and pad pockets which have been suitably matched.

Further objects and features of invention will be apparent from the detailed description of a preferred embodiment with reference to the accompanying drawings, in which:

BRIEF DESCRIPTION OF THE DRAWINGS

For sake of clarity and to provide figures in a more enlarge scale only one half, the right half, is shown.

DESCRIPTION OF THE PREFERRED EMBODIMENT

Figure 1:
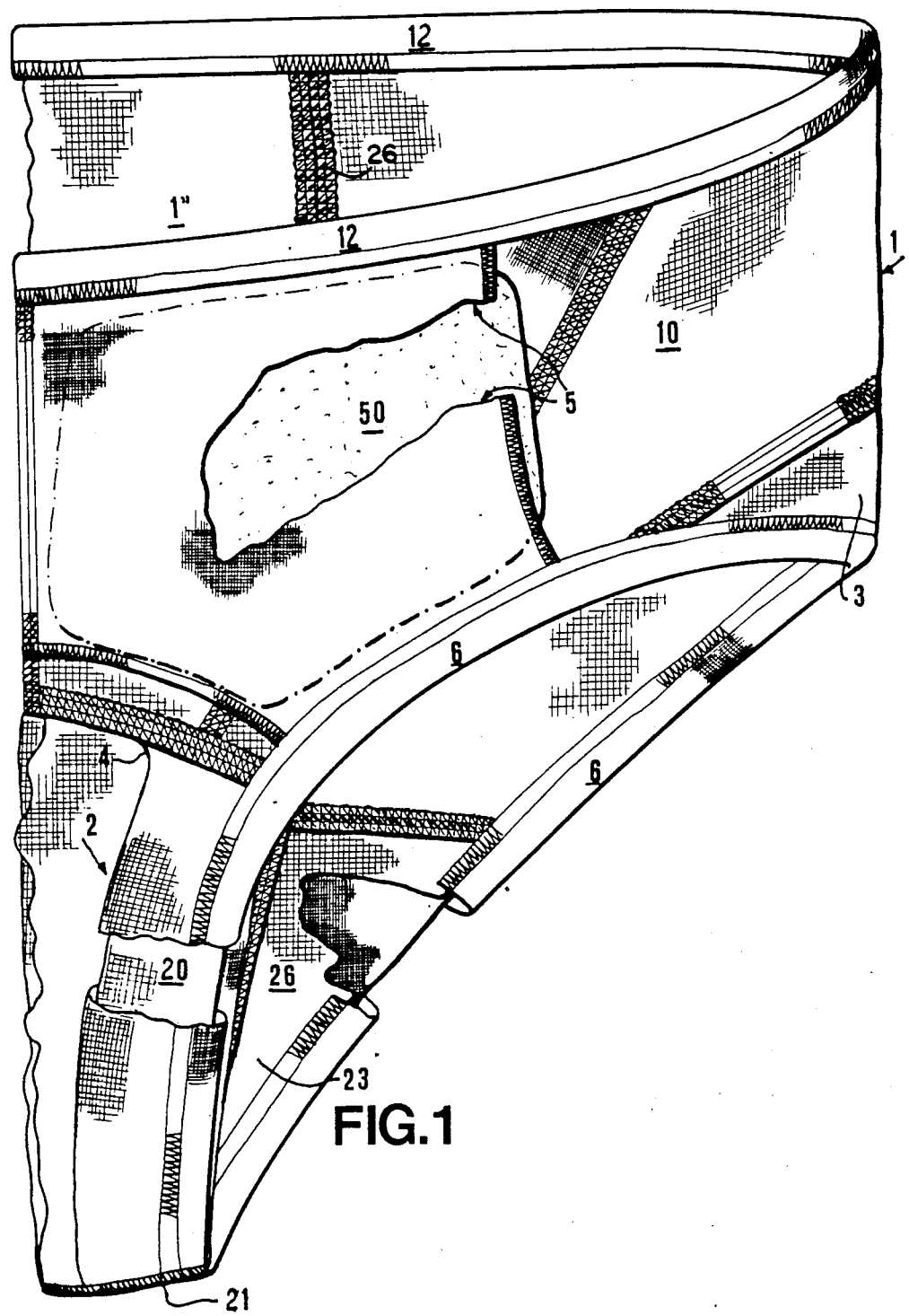
FIG. 1 is a perspective front view of a pants-like undergarment half according to the present invention wherein, for sake of clarity and completion, layers and portion thereof have been broken away.
Figures 2, 4:
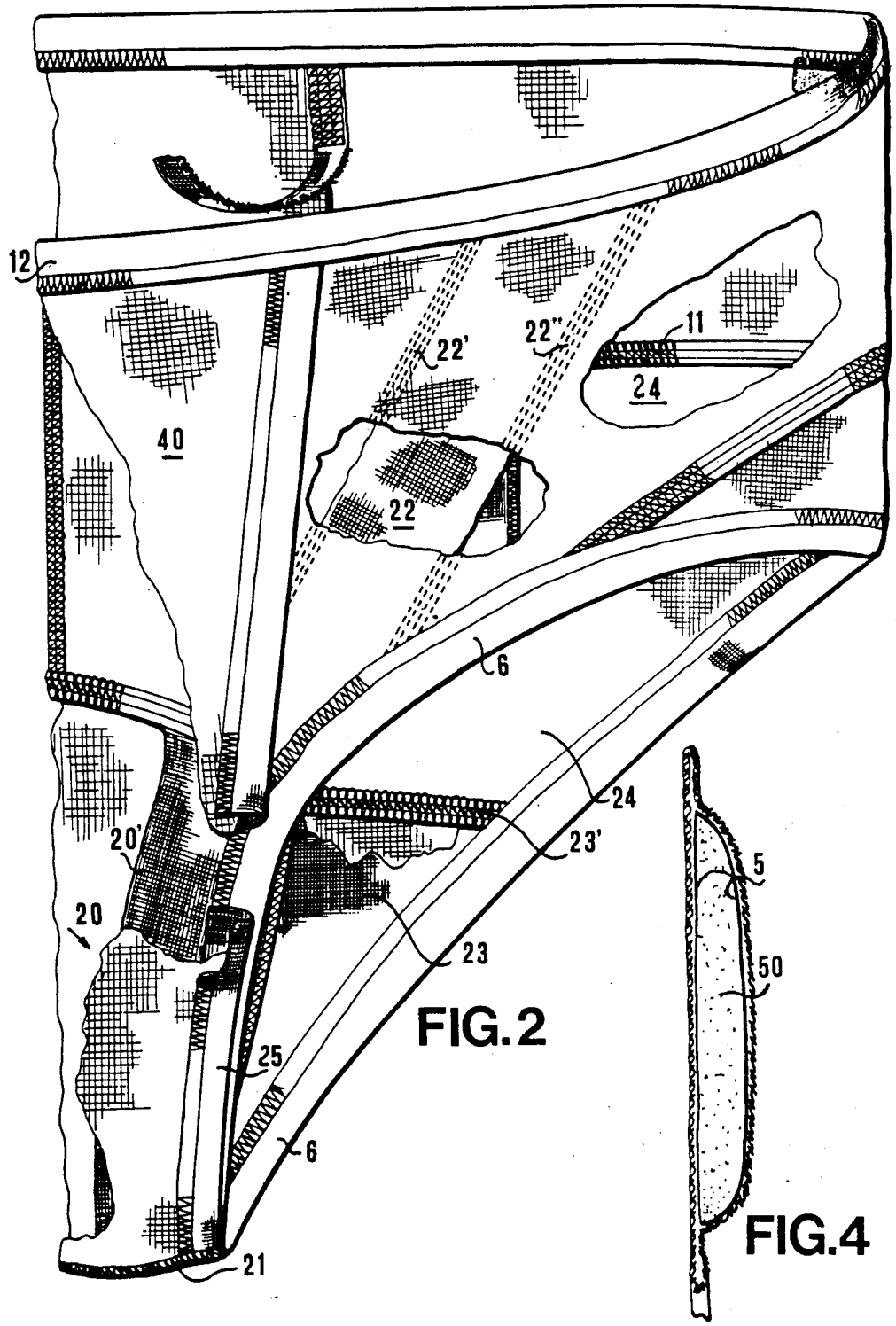
FIG. 2 is substantially a repetition of FIG. 1 here the sections broken away and those shown are different therefrom.
FIG. 4 is a cross-section of a portion of FIG. 1.
Figure 3:
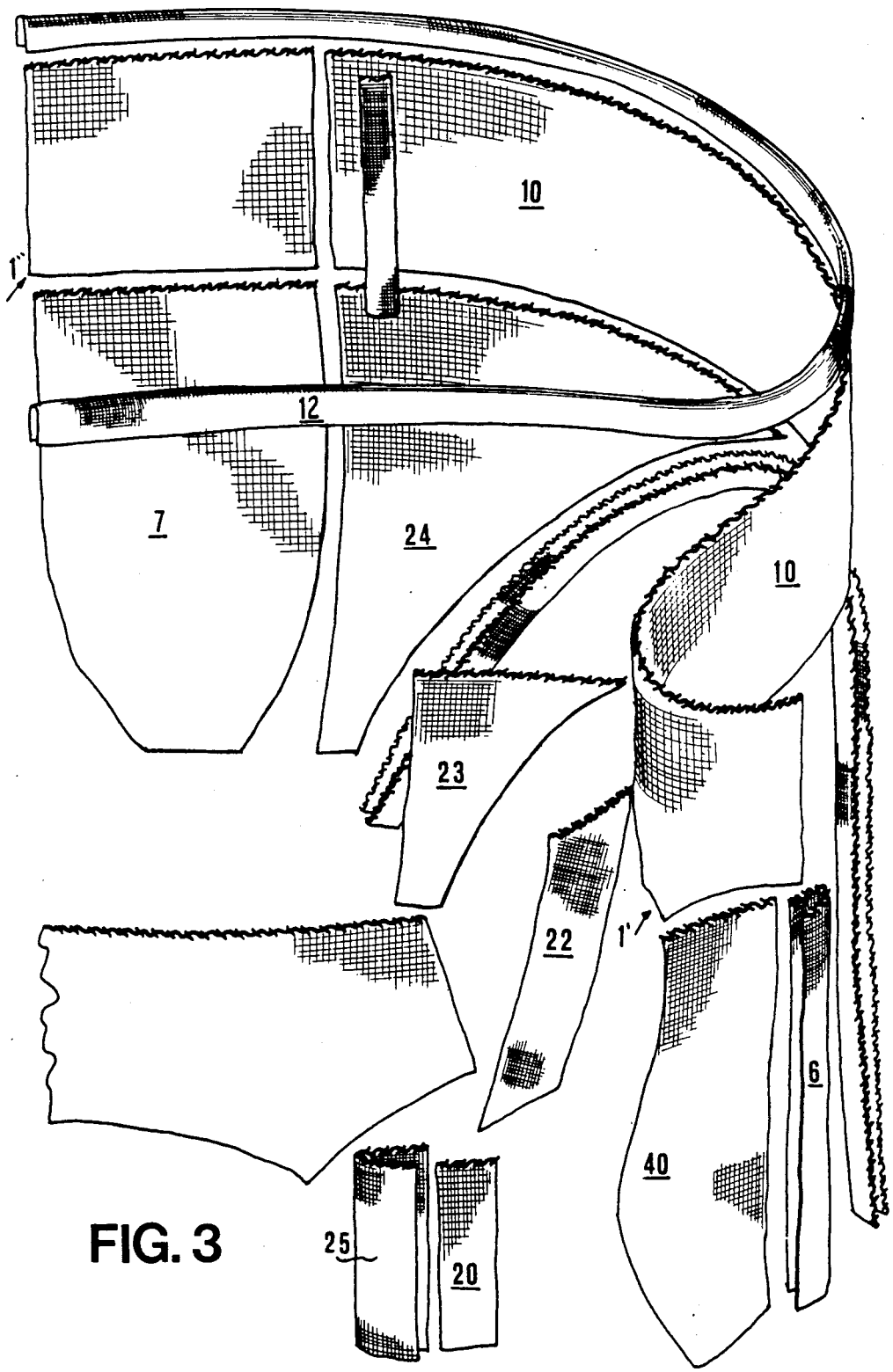
FIG. 3 is a perspective view of a slip half, according to the present invention, exploded in its components.

Referring to the drawings, an elastic pants-like undergarment, serving as a truss, comprises conventionally a belt 1, substantially involving, at least forwardly, the hernia affectable critical region and an elastic intersewn structure, comprising an undercrotch 2. At the edge of these components there are two upper girdles, not shown, which may comprise a single piece with the belt 1, while at the bottom on the sides 3 there are wide bands (not shown) which may provide a single piece with belt 1 and/or the upper girdle. In a conventional elastic pants-like undergarment, serving as a truss, substantially in one piece the elastic intersewn structure is provided substantially by overlapping the elastic components whereby to increase its retaining effect. The covering 40 for opening 4 for genitals is completely flat whereby it continuously bears heavily against genitals.

Whereas according to the present invention the belt 1 is drastically reduced to include, at least forwardly, only the hernia affectable critical region. According to an embodiment the present invention, belt 1 is made of elastic multiextensible cloth or fabric 10, strongly elastic, i.e., appropriate to provide on reduced areas concentrated intense pressures, further stressed by use, in appropriate pockets 5, of pressing pads 50. Reasons of practice suggest sharing of same belt in three sections 1, 1', 1''. Of course belt 1 is provided with an upper hem 12, made of elastic cloth or fabric and possibly of multiextensive kind. Whereas, at the bottom, it is delimited by sewing 11, preferably a sewing made with a multineedle sewing machine with stain stitch and covering on both sides and provided with an elastic thread, forwardly broken whereby to receive hems 6 to which it is joined and of which more will be spoken later on. Belt 1 comprises the main component of truss intersewn structure. Again according to the present invention, it is made by elastic and inextensible components possibly embodied in belt 1. In fact, the same intersewn structure, provides substantially two undercrotches 2, each including a connection, which starting from the upper rim 12 with an inextensible reinforcement 22 is sided therealong by sewing 22'' and with vertical trend descends, crossing the belt 1. The inextensible reinforcements 22, join, substantially to the groin covering segment 20, of elastic material, reaching the undercrotch center 21, whereby to comprise thereafter, in the rear side, an inextensible strip 23, sewn at 23', and an anatomic piece 24 of elastic fabric intersewn by id sewing 11 to belt 1. As regards the consistency of undercrotches 2 an inextensible segment 22 thereof comprises in the rear wall of the forward side a ribbon 22 of inextensible fabric. Whereas, the segment 20 comprises an inner core 20' of an elastic strong fabric covered on both sides by an elastic tape 25 made of soft fabric. The segment 20 is connected, through the crotch center sewing 21, to the piece 23 of fabric which, as aforesaid, is inextensible and made of soft and thin fabric. Thereafter a soft piece of fabric 24 with an average elasticity is provided. Along the arch provided by undercrotches and at the centre thereof there are, in the central front side, excluding the belt portion 1, an opening 4 for genitals and, in the rear side, a piece 7 of very soft elastic fabric, providing, together with pieces of fabric 23 and 24, connected thereto by sewing 26, an anatomic covering which, in the upper side, is connected to the section 1'' of the belt 1, by sewing 11. Laid upon the middle forward section of belt 1 and opening 4, with connections at the upper hem 12 and at the bottom hem, there is a bag, provided by two fabric strips, which are sewn in an anatomic fashion, to receive the genitals. According to a preferred embodiment of the present invention, the same strips are made of very soft elastic fabric, so as to provide a genital gentle suspending action. As aforesaid each hem 6 is joined with its middle part to the bottom edge of belt 1 and extends with one of its ends to the crotch center sewing 21 which connects the forward components and backward components, theretogether, viz.: the ends of hems 6, the body of hems 6, the strips 23 and 7, the crotch coverings 20, 20' and 25 and the suspender strips 40. Whereas, its other end is sewed to the upper hem 12 after having rimmed the whole leg opening edge. On the rear side of front part of the belt 1 in supposed defective areas, where hernia may protrude, pockets 5 are provided which are characterized by a side opening for a possible centripetal introduction of one or more pads 50. From the aforesaid it will be appreciated that the belt 1 is extremely reduced and limited to the heria affectable critical region and that the retaining structures, substantially provided by undercrotches are connected to the same belt by crossing it. An arrangement is provided in connection with opening 4 for genitals whereby they are not stressed by elastic means; they are nested in the bag provided by strips 40 and access to them, from the sides thereof, is at once gained with abundant facility. The retaining effectiveness of undercrotches comprising segments 22, 20, 23 and 24 is obtained, in the whole, by intercalation of inextensible, strongly elastic, ordinarily elastic and slightly elastic components, thereby resulting in utmost local effectiveness. The rear side, whose function is covering, is substantially without roughness and multiply clothes which may disturb the wearer in delicate areas. In fact, to cover the glutaei the utmost soft cloth or fabrics are used and they comprise an anatomical or three dimensional shape. In conclusion, the therapeutical garment is almost like pants, providing the typical functions thereof and involves areas of the human body that usually have substantially constant sizes and shapes. Consequently, such involved region, is necessary and sufficient to provide usual and retaining functions and any extension, included in conventional pants, may be obviated, whereby not to disturb, with useless stresses, running of physiological functions in parts of the human body not specifically involved by the appliance.

It is to be understood that the embodiments of the invention which have been described are merely illustrative of the principle of the invention. Numerous modifications may be made without departing from the true spirit and scope of the invention.

I claim:

1. A combination underpant and hernial truss comprising:
   an underpant brief having a circumferential upper edge, a front portion, a rear portion, a crotch portion, and spaced leg holes separated by said crotch portion;
   an elastic belt disposed at said circumferential upper edge of said underpant and substantially continuously affixed to said brief at its circumference said elastic belt being dimensioned to cover only a hernia affectable critical region; and
   a pair of at least partly elastic undercrotch bands each having a pair of ends fixedly secured to said belt and passing laterally of said crotch portion and adjacent said leg holes of said brief;
   said elastic belt girdling a hernia affectable region of a wearer and an inelastic crotch portion extending between said undercrotch bands.

2. The invention according to claim 1, wherein said undercrotch bands each comprise an elastic segment and an inelastic segment joined thereto, said inelastic segment being disposed adjacent said hernia affectable region of said wearer.

3. The invention according to claim 1, further comprising a retaining pad pocket positioned adjacent said hernia affectable region of said wearer.

4. The invention according to claim 2, wherein said inelastic segment of said undercrotch band extends diagonally across said hernia affectable region of said wearer.

5. The invention according to claim 2, wherein said elastic segment of said undercrotch band is disposed adjacent an inguinal channel of said wearer.

6. The invention according to claim 5, wherein said elastic segment is strongly elastic and laterally narrow but relatively thick in cross section.

7. The invention according to claim 1, wherein said undercrotch bands each further comprise a second inextensible segment extending rearwardly upwardly from said elastic segment and connected to it adjacent an inguinal channel of said wearer.

8. The invention according to claim 7, wherein said second inextensible segment is constructed of soft cloth.

9. The invention according to claim 7, wherein said undercrotch bands each further comprise a second moderately elastic segment extending upwardly from said second inextensible segment and connected to said belt at said rear of said underpant.

10. The invention according to claim 1, further comprising an opening in said crotch portion for the genitals of said wearer.

11. The invention according to claim 1, wherein said underpant and said bands are dimensioned so as to provide a three dimensional relief shape on the rear of said underpant brief, conforming to the glutei of said wearer.

12. The invention according to claim 1, wherein said underpant rear comprises a piece of cloth extending between said bands.

13. The invention according to claim 12, wherein said rear cloth piece is configured in the shape of a shield.

14. The invention according to claim 1, wherein said crotch portion of said underpant comprises a front elastic cloth piece extending between said bands.

15. The invention according to claim 1, wherein said crotch portion of said underpant comprises a pair of cloth pieces having affixed top and bottom edges, and side edges substantially unaffixed to one another.

16. The invention according to claim 3, wherein said pocket includes a lateral opening.

* * * * *